US012383142B2

(12) United States Patent
Kamon

(10) Patent No.: US 12,383,142 B2
(45) Date of Patent: Aug. 12, 2025

(54) MEDICAL IMAGE PROCESSING APPARATUS, MEDICAL IMAGE PROCESSING METHOD, AND PROGRAM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 391 days.

(21) Appl. No.: 17/857,419

(22) Filed: Jul. 5, 2022

(65) Prior Publication Data

US 2022/0330825 A1 Oct. 20, 2022

Related U.S. Application Data

(63) Continuation of application No. PCT/JP2021/002354, filed on Jan. 25, 2021.

(30) Foreign Application Priority Data

Jan. 27, 2020 (JP) ................................. 2020-010917

(51) Int. Cl.
*A61B 5/00* (2006.01)
*A61B 8/12* (2006.01)

(52) U.S. Cl.
CPC .............. *A61B 5/0066* (2013.01); *A61B 8/12* (2013.01)

(58) Field of Classification Search
CPC ........... A61B 6/12; A61B 6/463; A61B 6/469; A61B 5/0066; A61B 1/00009; A61B 1/00055
See application file for complete search history.

(56) References Cited

U.S. PATENT DOCUMENTS 11,871,903 B2 * 1/2024 Iwaki ................... A61B 1/0005
2008/0004506 A1 * 1/2008 Ikeda ..................... A61B 6/032
600/300

(Continued)

FOREIGN PATENT DOCUMENTS

CN 105848559 A 8/2016
CN 110663251 A 1/2020

(Continued)

OTHER PUBLICATIONS

An Office Action; "Notice of Reasons for Refusal," mailed by the Japanese Patent Office on Jul. 8, 2024, which corresponds to Japanese Patent Application No. 2021-574003 and is related to U.S. Appl. No. 17/857,419; with English language translation.

(Continued)

Primary Examiner — Daniel G Mariam
(74) Attorney, Agent, or Firm — Studebaker Brackett PLLC

(57) ABSTRACT

Provided are a medical image processing apparatus and a medical image processing method that effectively display an observation state indication related to the comprehensiveness of observation while suppressing a decrease in the visibility of an endoscopic image. The medical image processing apparatus is a medical image processing apparatus including a processor and a memory. The processor is configured to acquire a plurality of medical images in a time-series manner, make a determination of an observation state in units of a small area of a photographic subject on the basis of the medical images, cause the memory to store a result of the determination, and upon an observation state of the photographic subject being changed, cause a monitor to display an observation state indication of the photographic subject, the observation state indication being based on the result of the determination stored in the memory.

16 Claims, 10 Drawing Sheets

(56) References Cited

U.S. PATENT DOCUMENTS

| | | |
|---|---|---|
| 2015/0313445 A1 | 11/2015 | Davidson et al. |
| 2016/0323514 A1 | 11/2016 | Tsuchiya et al. |
| 2018/0084970 A1 | 3/2018 | Harada et al. |
| 2018/0098690 A1* | 4/2018 | Iwaki ............... A61B 1/05 |
| 2019/0043215 A1 | 2/2019 | Ito et al. |
| 2020/0065970 A1* | 2/2020 | Sonoda ............ A61B 1/0005 |
| 2020/0069160 A1 | 3/2020 | Oosake |
| 2021/0098089 A1* | 4/2021 | Choi ............... G16H 50/20 |
| 2021/0106208 A1 | 4/2021 | Iwaki |

FOREIGN PATENT DOCUMENTS

| | | |
|---|---|---|
| JP | 2016-002206 A | 1/2016 |
| JP | 6211239 B1 | 10/2017 |
| JP | 2018-050890 A | 4/2018 |
| JP | 6632020 B1 | 1/2020 |
| WO | 2016/199273 A1 | 12/2016 |
| WO | 2017/203814 A1 | 11/2017 |
| WO | 2018/221033 A1 | 12/2018 |
| WO | 2019/244255 A1 | 12/2019 |

OTHER PUBLICATIONS

"Notice of Reasons for Refusal" Office Action issued in JP 2021-574003; mailed by the Japanese Patent Office on Jul. 11, 2023.

The extended European search report issued by the European Patent Office on Jun. 12, 2023, which corresponds to European Patent Application No. 21748213.2-1126 and is related to U.S. Appl. No. 17/857,419.

An Office Action; "Notice of Reasons for Refusal," mailed by the Japanese Patent Office on Jan. 17, 2024, which corresponds to Japanese Patent Application No. 2021-574003 and is related to U.S. Appl. No. 17/857,419; with English language translation.

International Search Report issued in PCT/JP2021/002354; mailed Mar. 23, 2021.

International Preliminary Report On Patentability and Written Opinion issued in PCT/JP2021/002354; issued Jul. 28, 2022.

"Decision of Dismissal of Amendment" Office Action issued in JP 2021-574003; mailed by the Japanese Patent Office on Dec. 13, 2024.

An Office Action; mailed by the China National Intellectual Property Administration of the People's Republic of China on Mar. 10, 2025, which corresponds to Chinese Patent Application No. 202180009915.7 and is related to U.S. Appl. No. 17/857,419.

* cited by examiner

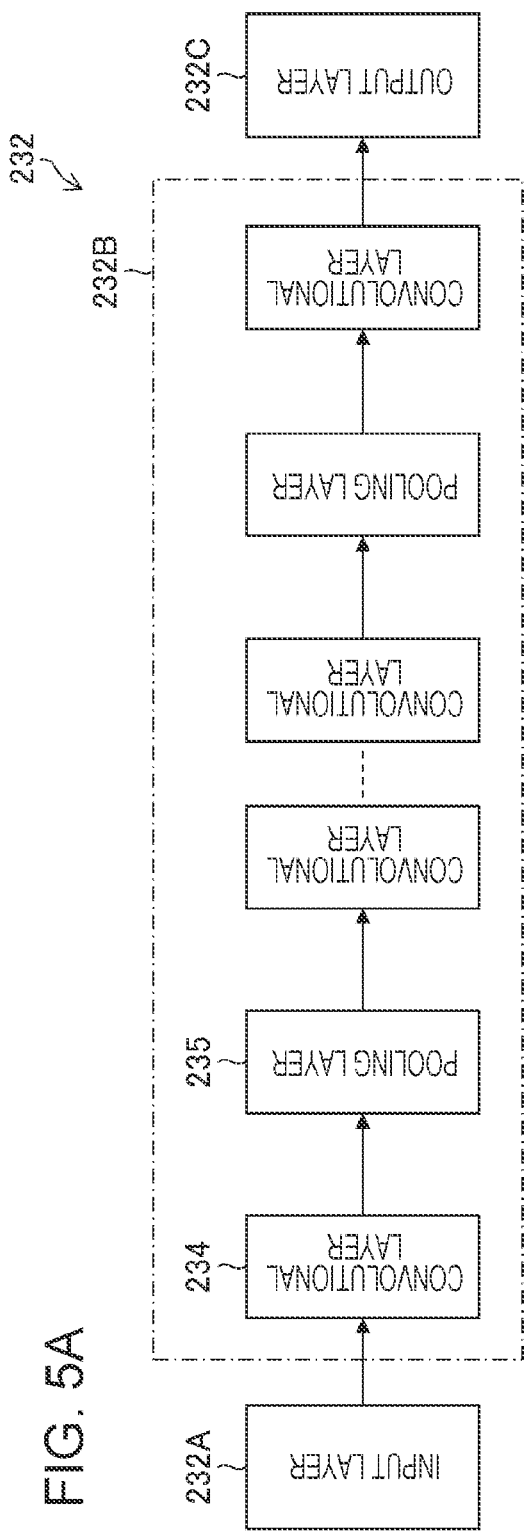
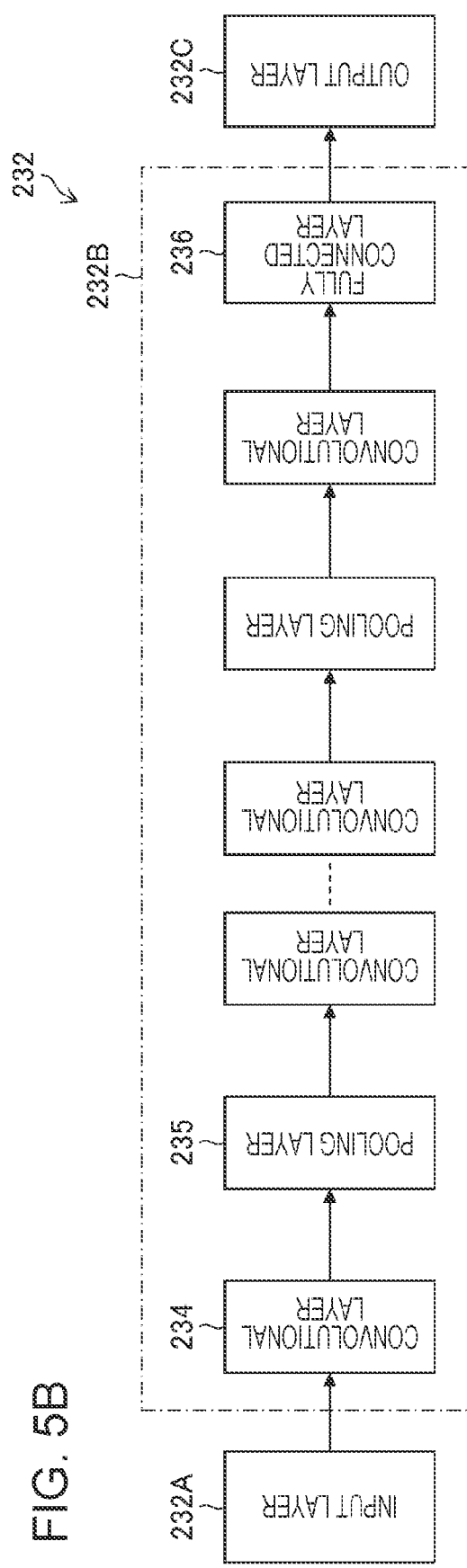

MEDICAL IMAGE PROCESSING APPARATUS, MEDICAL IMAGE PROCESSING METHOD, AND PROGRAM

CROSS-REFERENCE TO RELATED APPLICATIONS

The present application is a Continuation of PCT International Application No. PCT/JP2021/002354 filed on Jan. 25, 2021 claiming priority under 35 U.S.C § 119(a) to Japanese Patent Application No. 2020-010917 filed on Jan. 27, 2020. Each of the above applications is hereby expressly incorporated by reference, in its entirety, into the present application.

BACKGROUND OF THE INVENTION

1. Field of the Invention

The present invention relates to a medical image processing apparatus, a medical image processing method, and a program.

2. Description of the Related Art

Hitherto, it has been demanded to comprehensively observe an area of an organ or the like as a target to be examined in an examination performed using an endoscope system.

JP2018-50890A describes a technique aimed at preventing insufficient imaging in an examination using an endoscope system. In the technique described in JP2018-50890A, a map image depicting an imaged area and a not-yet-imaged area of a target organ to be imaged is displayed as a notification indication on a monitor.

SUMMARY OF THE INVENTION

Normally, an endoscopic image captured in real time during an examination is displayed in a main display region of a monitor of an endoscope system. Thus, in a case where a notification indication as that described in JP2018-50890A is displayed in the main display region, the notification indication is superimposed on the endoscopic image, and the visibility of the endoscopic image decreases. In a case where the notification indication is displayed in a sub display region of the monitor, the display region is small and thus the visibility of the notification indication decreases. On the other hand, the notification indication may be provided on a sub-monitor different from a main monitor. However, this involves an issue that a user is unable to concentrate his/her attention on an endoscopic image displayed on the main monitor during an examination.

The above-described JP2018-50890A does not refer to a display manner in which the visibility of an endoscopic image or the visibility of a notification indication (map image) is taken into consideration.

The present invention has been made in view of these circumstances, and an object of the present invention is to provide a medical image processing apparatus, a medical image processing method, and a program that effectively display an observation state indication related to the comprehensiveness of observation while suppressing a decrease in the visibility of an endoscopic image.

A medical image processing apparatus according to an aspect of the present invention for achieving the above-described object is a medical image processing apparatus including a processor and a memory. The processor is configured to acquire a plurality of medical images in a time-series manner, make a determination of an observation state in units of a small area of a photographic subject on the basis of the medical images, cause the memory to store a result of the determination, and upon an observation state of the photographic subject being changed, cause a monitor to display an observation state indication of the photographic subject, the observation state indication being based on the result of the determination stored in the memory.

According to this aspect, upon the observation state of the photographic subject being changed, the observation state indication of the photographic subject is displayed on the monitor. Accordingly, as a result of displaying the observation state indication of the photographic subject at an appropriate timing, display can be effectively performed while an influence on observation of an endoscopic image is suppressed.

Preferably, the processor is configured to cause the observation state indication displayed on the monitor to be hidden after a predetermined time elapses.

Preferably, the medical image processing apparatus further includes a user operation acceptance unit, and the processor is configured to cause the observation state indication to be displayed or hidden on the basis of an instruction from the user operation acceptance unit.

Preferably, the processor is configured to, in a case of determining an observation state of the small area, determine that observation is completed in a case where observation of the small area has been completed, and determine that observation is uncompleted in a case where observation of the small area has not been completed.

Preferably, the processor is configured to cause the monitor to display the observation state indication by using text information.

Preferably, the processor is configured to provide the text information with information regarding completion or incompletion of observation of the unit of the small area of the photographic subject, and display, as the observation state indication, the text information provided with the information.

Preferably, the processor is configured to cause the observation state indication to be displayed by using a photographic subject model schematically representing the photographic subject.

Preferably, the processor is configured to provide the photographic subject model with information regarding completion or incompletion of observation of the unit of the small area of the photographic subject, and display, as the observation state indication, the photographic subject model provided with the information.

Preferably, the processor is configured to display, as the observation state indication, an indication indicating only completion of observation of the unit of the small area of the photographic subject or an indication indicating only incompletion of observation of the unit of the small area of the photographic subject.

Preferably, the processor is configured to cause the monitor to display the medical images such that the observation state indication is superimposed on the medical images.

Preferably, the processor is configured to cause a monitor having a first display region and a second display region smaller than the first display region to display the observation state indication in the first display region and the second display region in a manner different between the first display region and the second display region.

Preferably, the processor is configured to cause the observation state indication to be constantly displayed in the second display region.

Preferably, the processor is configured to cause a monitor having the first display region and a third display region different from the second display region to display the medical images in the third display region.

A medical image processing method according to another aspect of the present invention is a medical image processing method for a medical image processing apparatus including a processor and a memory. The processor is configured to execute a medical image acquisition step of acquiring a plurality of medical images in a time-series manner, an observation state determination step of making a determination of an observation state in units of a small area of a photographic subject on the basis of the medical images, a storage step of causing the memory to store a result of the determination, and a display step of, upon an observation state of the photographic subject being changed, causing a monitor to display an observation state indication of the photographic subject, the observation state indication being based on the result of the determination stored in the memory.

A program according to another aspect of the present invention is a program that causes a medical image processing apparatus including a processor and a memory to execute a medical image processing method. The processor is configured to execute a medical image acquisition step of acquiring a plurality of medical images in a time-series manner, an observation state determination step of making a determination of an observation state in units of a small area of a photographic subject on the basis of the medical images, a storage step of causing the memory to store a result of the determination, and a display step of, upon an observation state of the photographic subject being changed, causing a monitor to display an observation state indication of the photographic subject, the observation state indication being based on the result of the determination stored in the memory.

According to the present invention, an observation state indication of a photographic subject is displayed on a monitor upon an observation state of the photographic subject being changed. Thus, as a result of displaying the observation state indication of the photographic subject at an appropriate timing, effective display can be performed while an influence on observation of an endoscopic image is suppressed.

BRIEF DESCRIPTION OF THE DRAWINGS

FIGS. 5A and 5B are diagrams illustrating configurations of a neural network;

DESCRIPTION OF THE PREFERRED EMBODIMENTS

Hereinafter, preferred embodiments of a medical image processing apparatus, a medical image processing method, and a program according to the present invention will be described with reference to the attached drawings.

Configuration of Endoscope System

Figure 1:
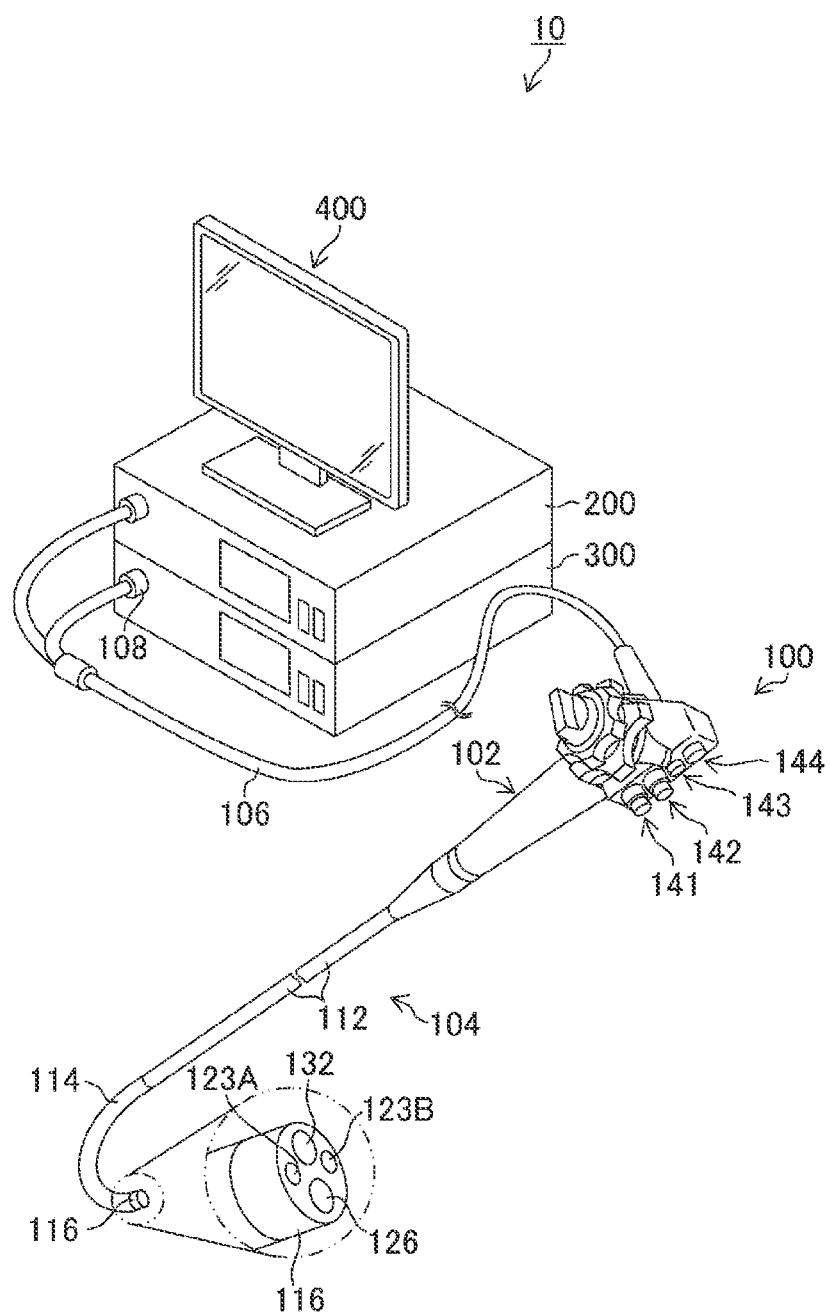
FIG. 1 is an external appearance diagram of an endoscope system.
Figure 2:
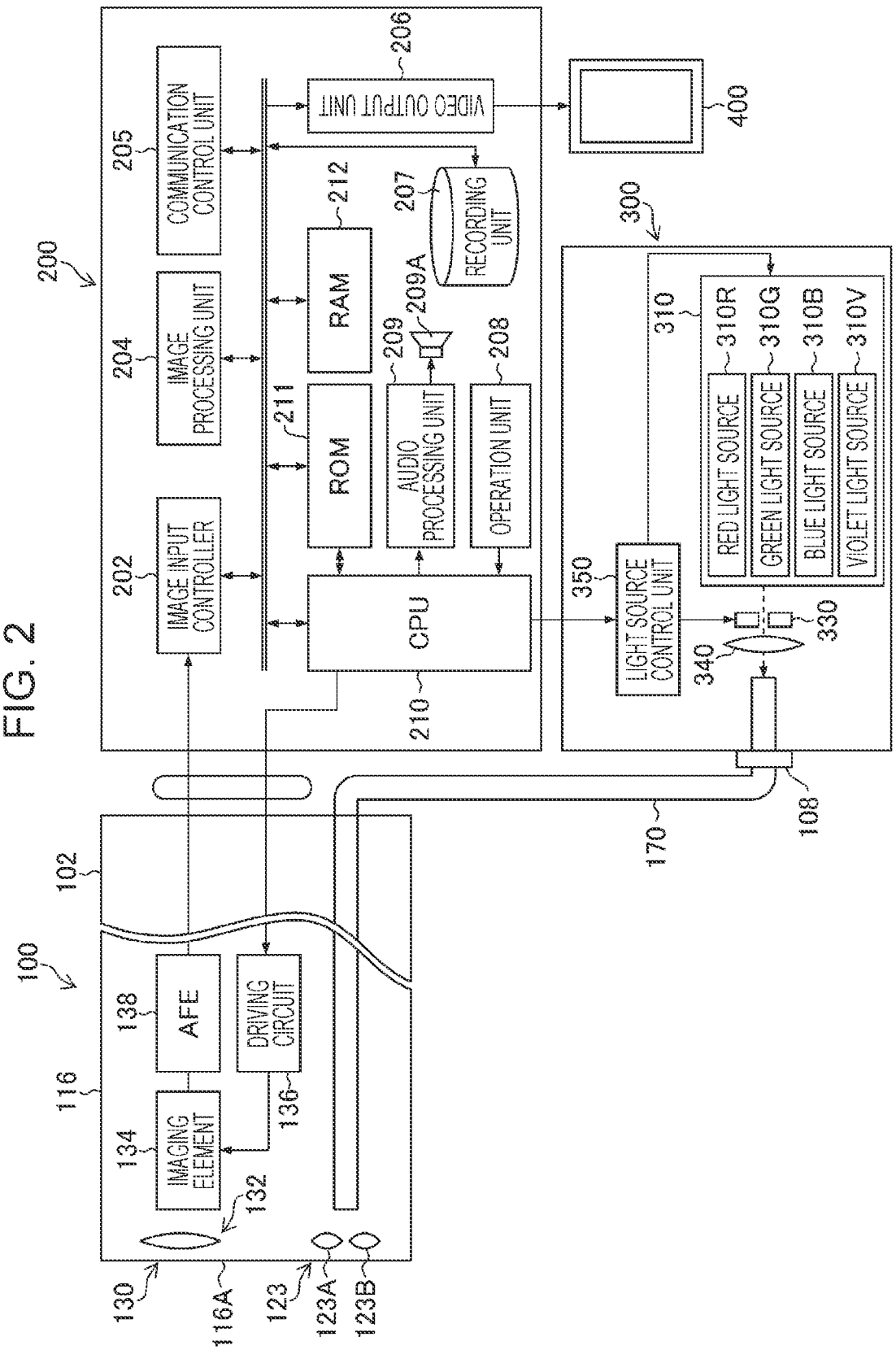
FIG. 2 is a block diagram illustrating the configuration of a main part of the endoscope system.

FIG. 1 is an external appearance diagram of an endoscope system 10, and FIG. 2 is a block diagram illustrating the configuration of a main part of the endoscope system 10. As illustrated in FIGS. 1 and 2, the endoscope system 10 is constituted by an endoscope 100, an endoscope processor apparatus 200, a light source apparatus 300, and a monitor 400. The endoscope processor apparatus 200 has the medical image processing apparatus of the present invention mounted therein.

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation and treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIG. 1 and FIG. 2, the imaging lens 132 is disposed on a distal-end-side surface 116A of the tip rigid part 116. An imaging element 134 of a complementary metal-oxide semiconductor (CMOS) type, a driving circuit 136, and an analog front end (AFE) 138 are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. The imaging element 134 may be of a charge coupled device (CCD) type. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the endoscope processor apparatus 200 through a signal cable that is not illustrated, and converted into a video signal. Accordingly, an endoscopic image (medical image) of the subject is displayed on the monitor 400, which is connected to the endoscope processor apparatus 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging at a determined frame rate while inserting or removing the endoscope 100 having the above-described configuration into or from a living body as a subject, thereby being capable of sequentially capturing time-series endoscopic images of the inside of the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, an endoscopic image having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type, area, purpose of observation, or the like of a photographic subject. It is also preferable that, during observation, the wavelengths of observation light be combined and/or switched in accordance with the type, area, purpose of observation, or the like of a photographic subject. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Endoscope Processor Apparatus

The configuration of the endoscope processor apparatus 200 will be described with reference to FIG. 2. In the endoscope processor apparatus 200, an image input controller 202 receives an image signal output from the endoscope 100, an image processing unit 204 performs necessary image processing thereon, and a video output unit 206 outputs a resulting image signal. Accordingly, an endoscopic image is displayed on the monitor 400. These processing operations are performed under control by a central processing unit (CPU) 210. The CPU 210 functions as a processor of the medical image processing apparatus. A communication control unit 205 controls communication, for acquiring a medical image, with a hospital information system (HIS), a hospital local area network (LAN), and/or an external system or network that are not illustrated.

Functions of Image Processing Unit

The image processing unit 204 is capable of performing calculation of a feature quantity of an endoscopic image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit (not illustrated) that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit (not illustrated) that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as an endoscopic image. The above-described processing is performed under control by the CPU 210.

Furthermore, the image processing unit 204 has individual functions in the medical image processing apparatus as described below.

Figure 3:
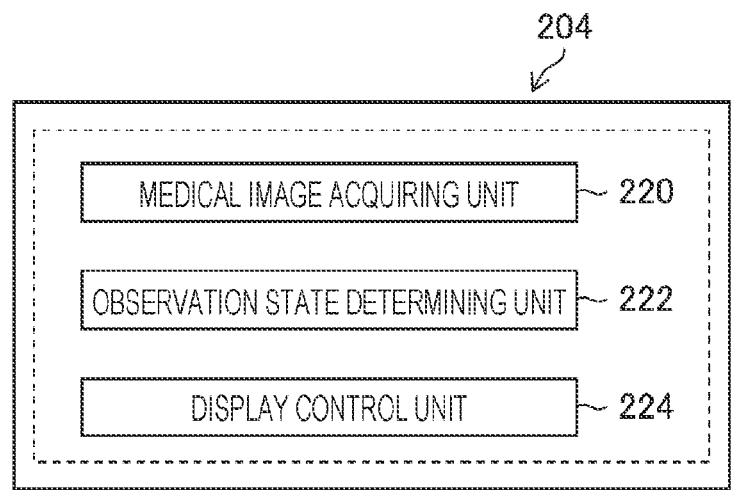
FIG. 3 is a functional block diagram of an image processing unit in a medical image processing apparatus.

FIG. 3 is a functional block diagram of the image processing unit 204 in the medical image processing apparatus. The image processing unit 204 includes a medical image acquiring unit 220, an observation state determining unit 222, and a display control unit 224.

Implementation of Functions by Various Types of Processors

The functions of the above-described units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as a read only memory (ROM) 211, and the computer refers to the software. The software stored in the non-transitory recording medium includes a program for executing the medical image processing method for the medical image processing apparatus according to the present invention, and data to be used to execute the program. The code may be recorded on a non-transitory recording medium, such as a magneto-optical recording device of various types or a semiconductor memory, instead of the ROM 211. In the processing using the software, a random access memory (RAM) 212 may be used as a transitory storage region, for example, and data stored in an electrically erasable and programmable read only memory (EEPROM) that is not illustrated can be referred to, for example. A recording unit 207 may be used as a "non-transitory recording medium".

The read only memory (ROM) 211 is a nonvolatile storage element (a non-transitory recording medium) and stores a computer-readable code of a program that causes the CPU 210 and/or the image processing unit 204 to execute various image processing methods. The random access memory (RAM) 212 is a storage element for temporary storage in various processing operations and can be used as a buffer when acquiring an image. An audio processing unit 209 outputs audio and sound from a speaker 209A under control by the CPU 210.

The operation unit 208 can be constituted by devices such as a keyboard and a mouse that are not illustrated. A user is able to provide an instruction to execute processing or designate a condition necessary for the execution via the operation unit 208.

Information Stored in Recording Unit

Figure 4:
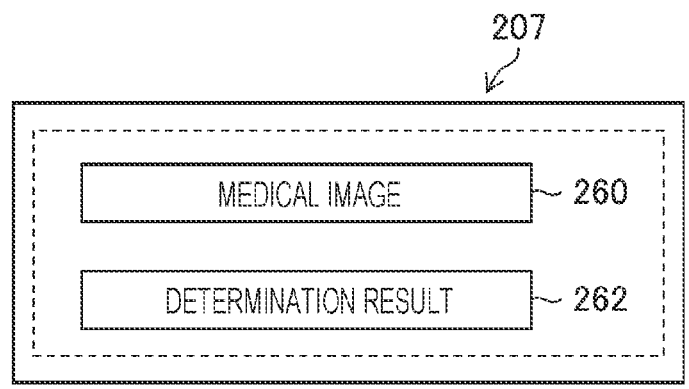
FIG. 4 is a diagram illustrating main information stored in a recording unit.

FIG. 4 is a diagram illustrating main information stored in the recording unit 207. The recording unit (memory) 207 stores a medical image (endoscopic image) 260, a determination result 262 of the observation state determining unit 222, and so forth. The recording unit 207 also stores information about a series of small areas to be observed in an examination performed using the endoscope system 10. The small areas of a photographic subject herein are, for example, individual portions of an organ. Specifically, in the case of performing an examination of observing all the portions of the stomach, the small areas are the cardia, fundus, angulus, gastric body (upper portion, middle portion, lower portion), antrum, anterior wall, posterior wall, greater curvature, and lesser curvature.

Recognizing Unit Using Neural Network

The observation state determining unit 222 in the above-described image processing unit 204 includes a recognizer. The recognizer is constituted by using a trained model (a model trained by using an image set constituted by captured images of a living body), such as a neural network, and is capable of recognizing small areas of a photographic subject. The observation state determining unit 222 determines, in units of a small area, whether observation of the small area has been completed, on the basis of the position of the small area recognized by the recognizer, the number of endoscopic images in which the small area has been recognized, or the like. Hereinafter, a description will be given of the configuration of the recognizer included in the observation state determining unit 222 in the case of using a convolutional neural network (CNN) as a neural network.

Example of Configuration of Recognizer

FIGS. 5A and 5B are diagrams illustrating configurations of a CNN 232 (neural network). In the example illustrated in FIG. 5A, the CNN 232 has an input layer 232A, an intermediate layer 232B, and an output layer 232C. The input layer 232A receives an endoscopic image acquired by the medical image acquiring unit 220 and outputs a feature quantity. The intermediate layer 232B includes convolutional layers 234 and pooling layers 235, and receives the feature quantity output from the input layer 232A and calculates another feature quantity. These layers have a structure in which a plurality of "nodes" are connected by "edges". Weighting coefficients applied to an input image are associated with the nodes and edges and are stored in a weighting coefficient storage unit that is not illustrated. The values of the weighting coefficients change as learning progresses.

Processing in Intermediate Layer

The intermediate layer 232B calculates a feature quantity through convolutional operation and pooling processing. The convolutional operation performed in the convolutional layer 234 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is reduced as convolution is performed in each layer in the case of being scaled down by convolution. The pooling processing performed in the pooling layer 235 is processing of reducing (or enlarging) the feature map output through the convolutional operation to create a new feature map, and plays a role in giving robustness so that the extracted feature is not affected by parallel movement or the like. The intermediate layer 232B can be constituted by one or a plurality of layers that perform these processing operations. The CNN 232 may be configured without a pooling layer 235.

The CNN 232 may include a fully connected layer 236 as in the example illustrated in FIG. 5B. The layer configuration of the CNN 232 is not limited to the configuration in which the convolutional layers 234 and the pooling layers 235 are alternately arranged, and may include a plurality of consecutive convolutional layers 234 or pooling layers 235 (for example, convolutional layers 234).

Figure 6:
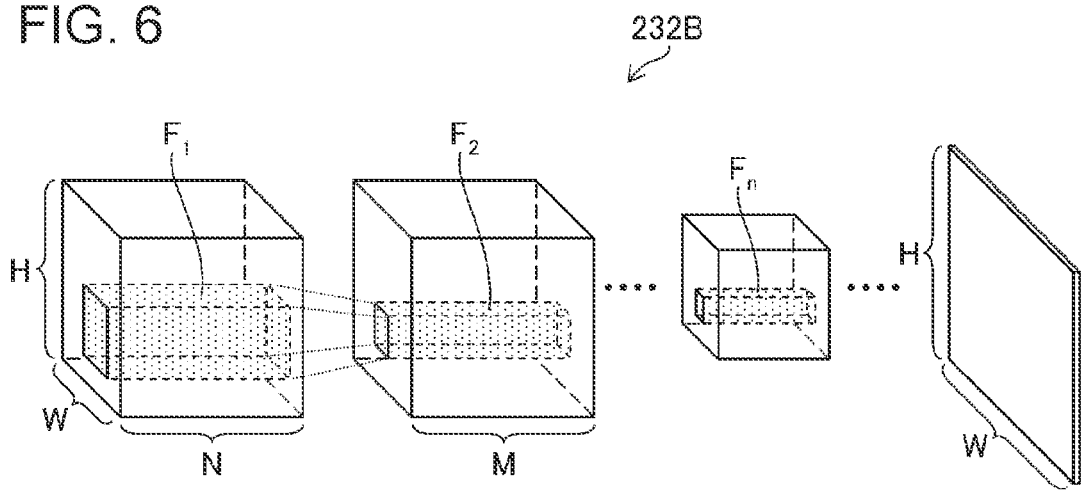
FIG. 6 is a schematic diagram illustrating an example configuration of an intermediate layer.

FIG. 6 is a schematic diagram illustrating an example configuration of the intermediate layer 232B of the CNN 232 illustrated in FIGS. 5A and 5B. In the first convolutional layer of the intermediate layer 232B, convolutional operation of an image set constituted by a plurality of endoscopic images and a filter $F_1$ is performed. The image set is constituted by N (N-channel) images each having an image size in which the height is represented by H and the width is represented by W. In the case of inputting normal-light images, the images constituting an image set are three-channel images of red (R), green (G), and blue (B). The filter $F_1$ convoluted with this image set has a filter size of 5×5×N in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of 3×3×M in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 232B, lower-order feature extraction (extraction of edges or the like) is performed in a convolutional layer near the input side, and higher-order feature extraction (extraction of features about the shape, structure, and the like of a recognition target) is performed near the output side.

The intermediate layer 232B may include a layer for performing batch normalization in addition to the convolutional layers 234 and the pooling layers 235. Batch normalization processing is the processing of normalizing a data distribution in units of mini batches for performing learning, and plays a role in quickly performing learning, reducing dependency on an initial value, suppressing overtraining, and so forth.

The output layer 232C outputs the feature quantity calculated by the intermediate layer 232B in a form appropriate for recognition. The output layer 232C may include a fully connected layer.

Individual Processes of Medical Image Processing Method

Next, a medical image processing method using the medical image processing apparatus will be described.

Figure 7:
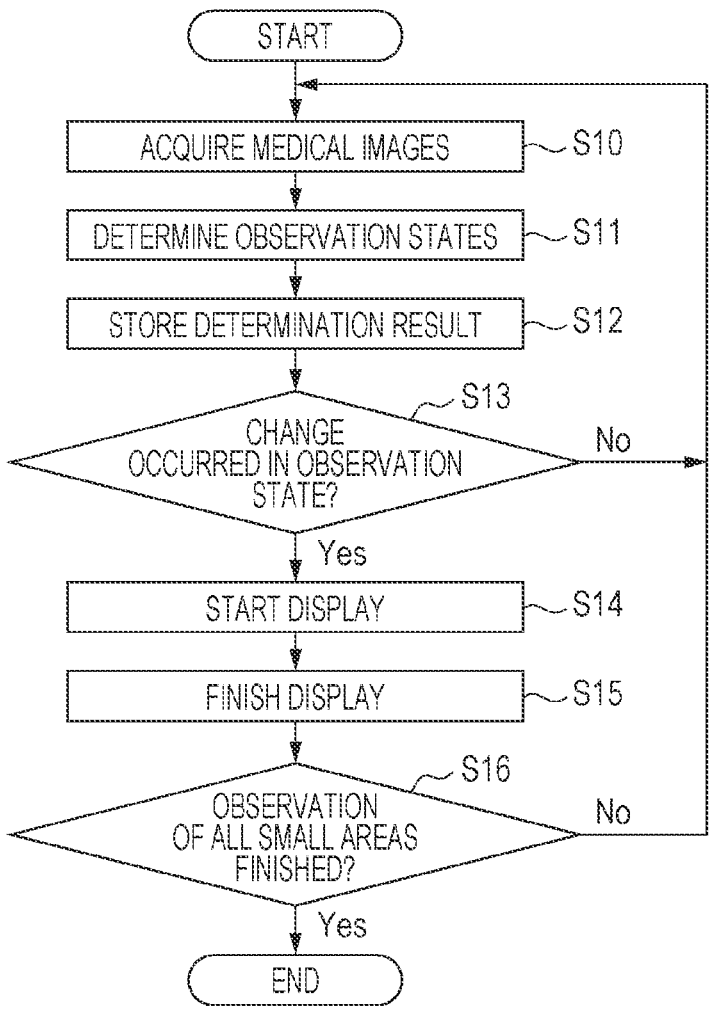
FIG. 7 is a flowchart illustrating a medical image processing method.

FIG. 7 is a flowchart illustrating a medical image processing method. Hereinafter, individual steps will be described with reference to FIG. 7. Hereinafter, a description will be given of the case of observing area 1, area 2, and area 3, which are small areas, in units of areas, for examining organ A as a photographic subject.

Medical Image Acquisition Step

The medical image acquiring unit 220 sequentially acquires a plurality of medical images of organ A in a time-series manner (step S10). The recording unit 207 stores a record indicating that observation of area 1, area 2, and area 3 of organ A is to be performed, and stores, in an initial state, a record indicating that observation of area 1, area 2, and area 3 has not been completed.

Observation State Determination Step

The observation state determining unit 222 determines, on the basis of the acquired medical images, the observation states of area 1, area 2, and area 3 of organ A (step S11). The observation state determining unit 222 recognizes area 1, area 2, or area 3 in the medical images. The observation state determining unit 222 then determines the observation states of area 1, area 2, and area 3 on the basis of a result of the recognition. For example, if area 1 has been recognized at the centers of ten chronologically consecutive medical images, the observation state determining unit 222 determines that observation of area 1 has been completed.

Storage Step

The recording unit 207 stores a result of the determination made by the observation state determining unit 222 (step S12). At start of the examination (initial state), a record indicating that observation of area 1, area 2, and area 3 has not been completed is stored. If the observation state determining unit 222 determines that observation of the individual areas has been completed, the record is updated to indicate that observation has been completed.

Display Step

The display control unit 224 determines whether a change has occurred in the observation state of the photographic subject (step S13). Upon determining that a change has occurred in the observation state of the photographic subject, the display control unit 224 causes the monitor 400 to display an observation state indication 501 of the photographic subject (step S14). Here, "upon the observation state of the photographic subject being changed" is a case where a change in the observation state has been stored in the recording unit 207 in a plurality of small area units that are stored in the recording unit 207 and that are to be observed. An example of the case is a case where the recording unit 207 stores a record indicating that observation of area 1, area 2, and area 3 has not been completed, then the observation state determining unit 222 determines that observation of area 1 has been completed, and then the observation state of area 1 has been changed to completion of observation in the recording unit 207. The observation state indication 501 of the photographic subject is an indication for notifying a user of the observation states of small area units constituting the photographic subject as an observation target. By viewing the observation state indication 501, the user is able to determine whether he/she is comprehensively observing small areas of the observation target.

Figure 8:
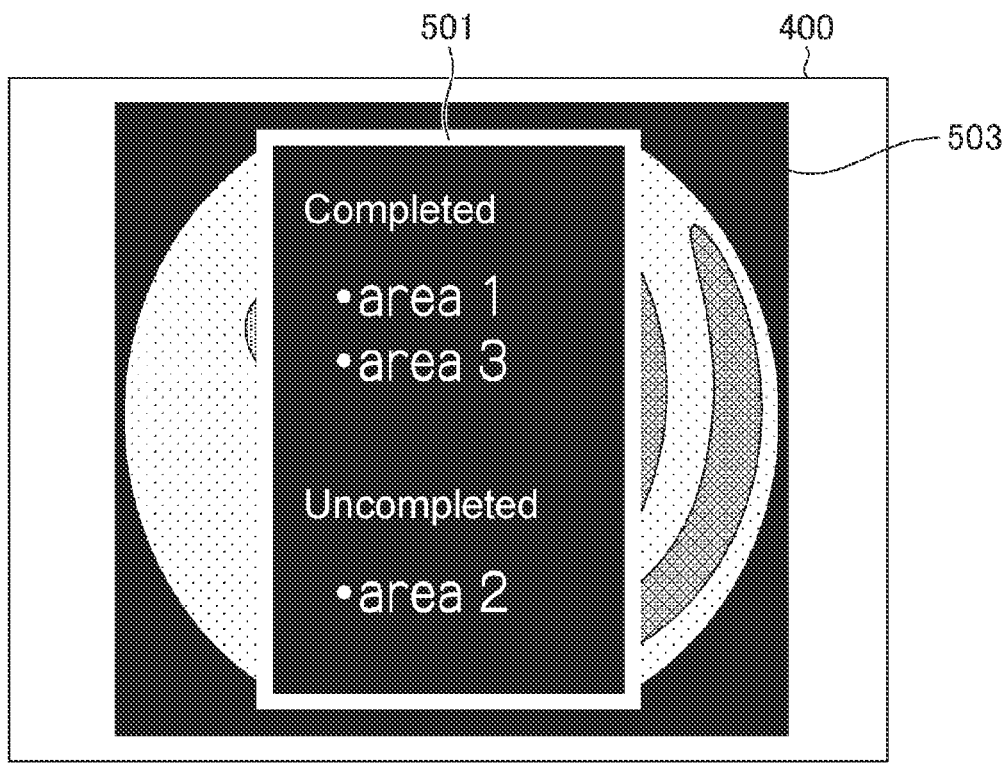
FIG. 8 is a diagram illustrating an example of an observation state indication.

FIG. 8 is a diagram illustrating an example of the observation state indication 501 of organ A displayed on the monitor 400.

In the case illustrated in FIG. 8, an endoscopic image 503 is displayed on the entire screen of the monitor 400. Upon the record in the recording unit 207 being updated from a record indicating that observation of area 3 has not been completed to a record indicating that observation of area 3 has been completed, the display control unit 224 causes the monitor 400 to display the observation state indication 501 such that the observation state indication 501 is superimposed on the endoscopic image 503. The observation state indication 501 is a list indication having text information indicating an area for which observation has been completed and an area for which observation has not been completed. In the observation state indication 501, area 1 and area 3 for which observation has been completed are shown below "Completed", and area 2 for which observation has not been completed is shown below "Uncompleted".

Referring back to FIG. 7, the display control unit 224 then continues displaying the observation state indication 501 until a predetermined display time elapses. The display time can be set by a user as appropriate. Preferably, the observation state indication 501 is hidden upon the observation state being checked by the user so that the endoscopic image 503 can be observed. Thus, it is preferable that the display time be set on the basis of a time within which the user is able to check the observation state. For example, the display time can be set to 10 seconds or 30 seconds. After that, the display control unit 224 hides the observation state indication 501 after the predetermined time has elapsed (step S15).

After that, the medical image acquiring unit 220 determines whether observation of all the small area units has been finished (step S16). Because observation of area 2 has not been completed, medical images are further acquired (step S10).

As described above, in the present invention, in the case of observing area 1, area 2, and area 3, which are small areas of organ A, the observation state indication 501 is provided upon the observation state of organ A being changed. Accordingly, as a result of providing the observation state indication 501 when it is necessary and hiding the observation state indication 501 in other cases, display can be effectively performed while an influence on observation of an endoscopic image is suppressed.

Modifications of Observation State Indication

In the example described in FIG. 8, a description has been given of the case of displaying the observation state indication 501 in which text information indicates an area for which observation has been completed and an area for which observation has not been completed. However, the example of the observation state indication 501 is not limited thereto. The display manner of the observation state indication 501 is not particularly limited as long as a user can be notified of an observation state of a photographic subject as an observation target by using text or a figure. Hereinafter, specific examples of the observation state indication 501 will be described.

Figure 9:
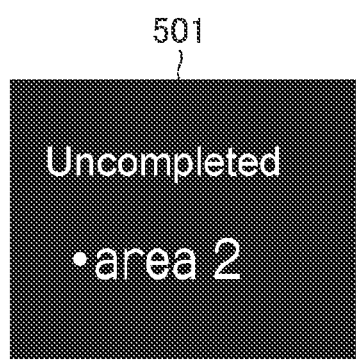
FIG. 9 is a diagram illustrating Modification 1 of an observation state indication.

FIG. 9 is a diagram illustrating Modification 1 of the observation state indication 501. The present modification is the observation state indication 501 using text information. The observation state indication 501 of the present modification indicates only an area for which observation has not been completed. Specifically, in a case where observation of area 2 has not been completed, text information indicating area 2 is shown below "Uncompleted".

In this way, as a result of providing the monitor 400 with the observation state indication 501 having only a small area for which observation has not been completed, the user is able to clearly recognize the small area for which observation has not been completed, and comprehensive observation can be realized. In the example in FIG. 9, a description has been given of an example of displaying, in the observation state indication 501, a small area for which observation has not been completed. However, a small area for which observation has been completed may be displayed in the observation state indication 501. In this case, the user is able to clearly recognize the small area for which observation has been completed.

Figure 10:
FIG. 10 is a diagram illustrating Modification 2 of an observation state indication.

FIG. 10 is a diagram illustrating Modification 2 of the observation state indication 501. The present modification is the observation state indication 501 using text information. In the observation state indication 501 of the present modification, all small areas (areas 1 to 5) constituting a photographic subject as an observation target are displayed in a list view. In the observation state indication 501, an area for which observation has been completed and an area for which observation has not been completed are displayed using characters of different colors. Specifically, in the observation state indication 501, areas 3 and 5 are displayed using characters of the same color because the observation thereof has not been completed, and areas 1, 2, and 4 are displayed using characters of the same color because the observation thereof has been completed. In this way, all the small areas are displayed in a list view, and text is provided with, in units of small areas, information indicating that observation has been completed or information indicating that observation has not been completed. Thus, the user is able to comprehensively recognize an area for which observation has been completed or has not been completed.

Figure 11:
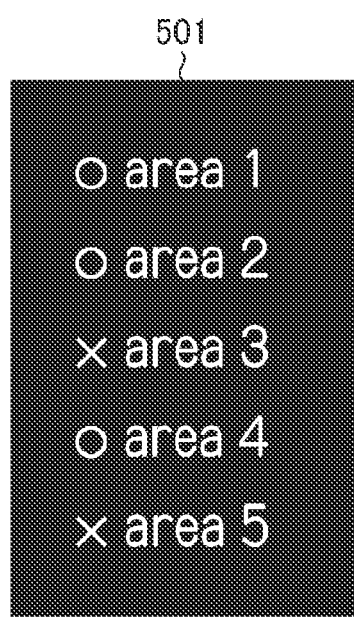
FIG. 11 is a diagram illustrating Modification 3 of an observation state indication.

FIG. 11 is a diagram illustrating Modification 3 of the observation state indication 501. The present modification is the observation state indication 501 using text information. In the observation state indication 501 of the present modification, all small areas (areas 1 to 5) constituting a photographic subject as an observation target are displayed in a list view. In the observation state indication 501, a circle and a cross are displayed beside an area for which observation has been completed and an area for which observation has not been completed, respectively. Specifically, in the observation state indication 501, areas 3 and 5 are given a cross because the observation thereof has not been completed, and areas 1, 2, and 4 are given a circle because the observation thereof has been completed. In this way, all the small areas are displayed in a list view, and information indicating that observation has been completed or information indicating that observation has not been completed is displayed beside text in units of small areas. Thus, the user is able to comprehensively recognize an area for which observation has been completed or has not been completed.

Figure 12:
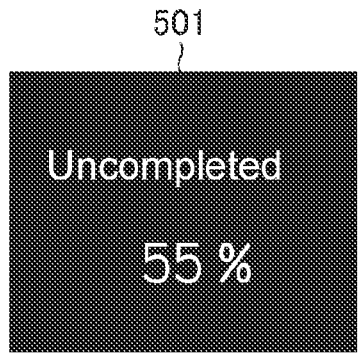
FIG. 12 is a diagram illustrating Modification 4 of an observation state indication.

FIG. 12 is a diagram illustrating Modification 4 of the observation state indication 501. The present modification is the observation state indication 501 using text information. In the observation state indication 501 of the present modification, a percentage of incompletion of observation is indicated as the observation state indication 501. The percentage of incompletion of observation herein means a percentage of small areas for which observation has not been completed among a plurality of small areas to be observed. The percentage may be calculated on the basis of the number of small areas or the area of small areas. In the example illustrated in FIG. 12, the percentage is indicated in a text form. Alternatively, the percentage may be indicated using a figure, such as a bar indicating the percentage. In this way, as a result of indicating the percentage of incompletion of observation, the user is able to clearly recognize the area for which observation has not been completed.

Figure 13:
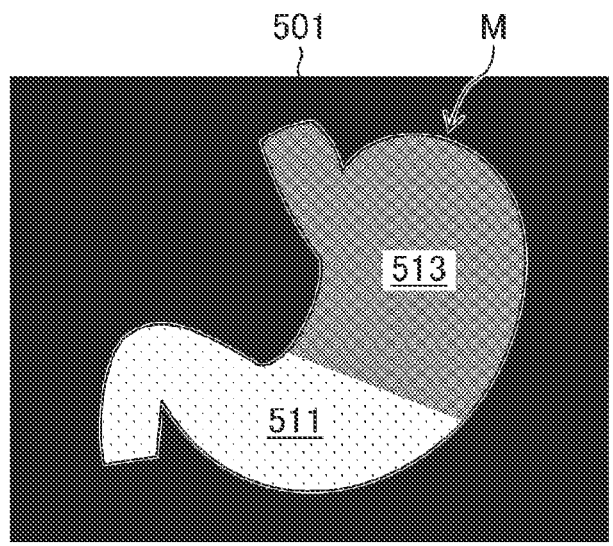
FIG. 13 is a diagram illustrating Modification 5 of an observation state indication.

FIG. 13 is a diagram illustrating Modification 5 of the observation state indication 501. The present modification is the observation state indication 501 using a photographic subject model M schematically representing a photographic subject. The photographic subject model M is a figure schematically illustrating the stomach, which is a photographic subject as an observation target. In the photographic subject model M, in small area units, an area 513 for which observation has been completed and an area 511 for which observation has not been completed are given different colors. In this way, as a result of providing the photographic subject model M with information indicating that observation has been completed and observation has not been completed, the user is able to recognize, in the photographic subject, the position of a small area for which observation has been completed and the position of a small area for which observation has not been completed. In the example illustrated in FIG. 13, information indicating that observation has been completed and observation has not been completed is provided by using different colors for areas of the photographic subject model M, but the present invention is not limited to this example. For example, information about completion of observation and incompletion of observation may be provided to the photographic subject model M by changing the density of a color.

Figure 14:
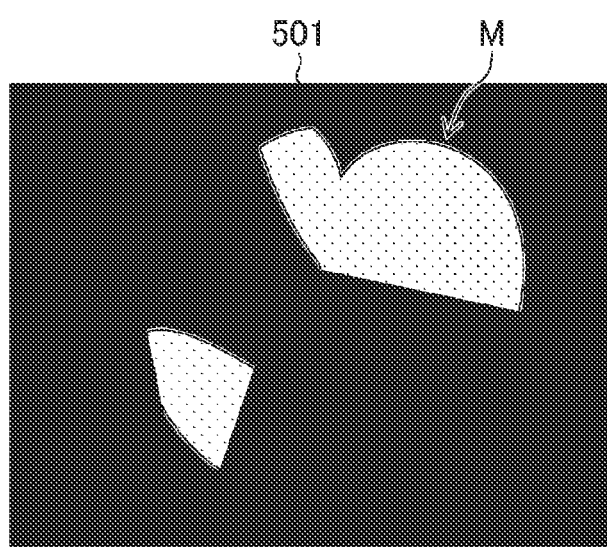
FIG. 14 is a diagram illustrating Modification 6 of an observation state indication.

FIG. 14 is a diagram illustrating Modification 6 of the observation state indication 501. The present modification is the observation state indication 501 using a photographic subject model M schematically representing a photographic subject. In the present modification, in the photographic subject model M, only a small area for which observation has been completed is shown. Upon observation of all the small areas being completed, the entire photographic subject model M (stomach) is displayed. In this way, as a result of providing the photographic subject model M with information indicating that observation has been completed and observation has not been completed, the user is able to recognize, in the photographic subject, the position of a small area for which observation has been completed and the position of a small area for which observation has not been completed. In FIG. 13 and FIG. 14, a sectional view of the stomach as a photographic subject is used as the photographic subject model M, but the present invention is not limited thereto. For example, the photographic subject model M may be a development view of the stomach as a photographic subject.

Modifications of Monitor

In the description given above, an example of the monitor 400 having only a main display region has been described, but the present invention is not limited thereto. Hereinafter, modifications of the monitor will be described.

Figure 15:
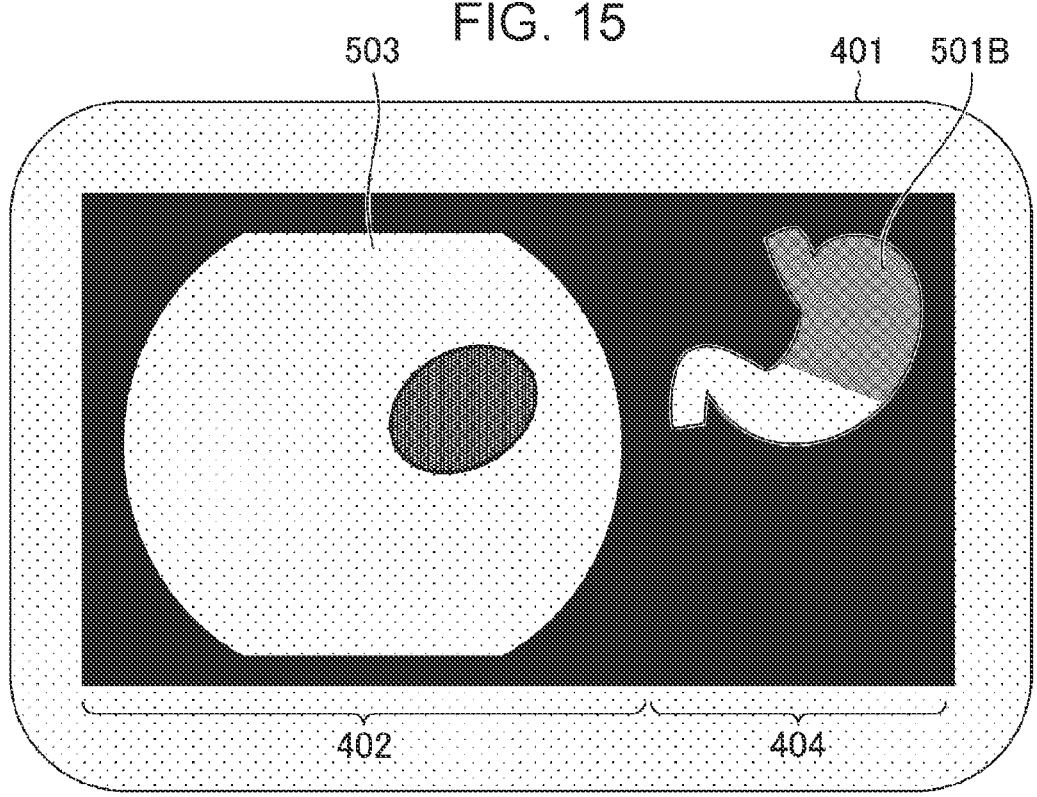
FIG. 15 is a diagram for describing an example of a monitor having a main display region and a sub display region.

FIG. 15 is a diagram for describing an example of a monitor 401 having a main display region and a sub display region.

As illustrated in FIG. 15, the monitor 401 has a main display region 402 and a sub display region 404. In the main display region 402, the endoscopic image 503 captured by the endoscope 100 is displayed in real time. The sub display region 404 is set to be smaller than the main display region 402, and information such as an imaging condition, a date, and patient information is displayed therein. In FIG. 15, illustration of these pieces of information displayed in the sub display region 404 is omitted. In the monitor 401, the observation state indication 501 is provided in the main display region 402 and the sub display region 404. In the main display region 402, the observation state indication 501 is displayed upon the observation state of a photographic subject being changed, and display is finished after a display time elapses, as described above. FIG. 15 illustrates a case where the observation state indication 501 is hidden in the main display region 402.

In the sub display region 404, an observation state indication 501B is constantly displayed. The sub display region 404 has a small display area. Thus, the observation state indication 501B is smaller than an observation state indication 501A displayed in the main display region 402, but serves as support for performing comprehensive observation. The same observation state indication or different observation state indications may be displayed in the main display region 402 and the sub display region 404.

Figure 16:
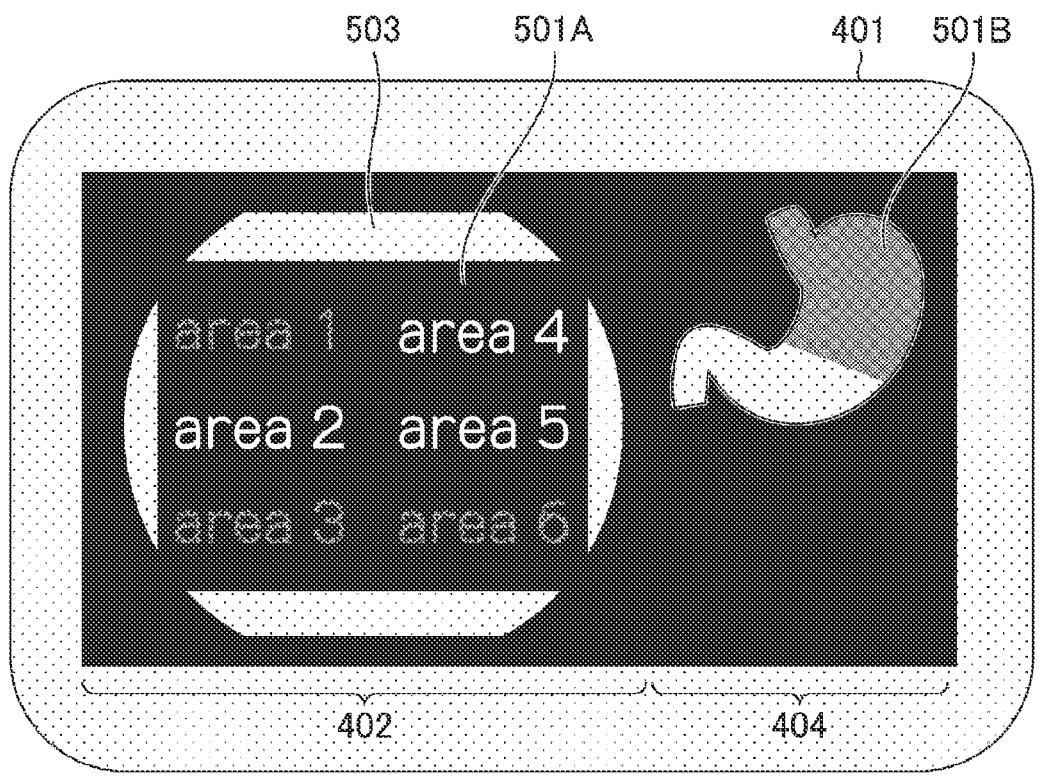
FIG. 16 is a diagram for describing an example of the case of displaying different observation state indications in the main display region and the sub display region.
Figure 17:
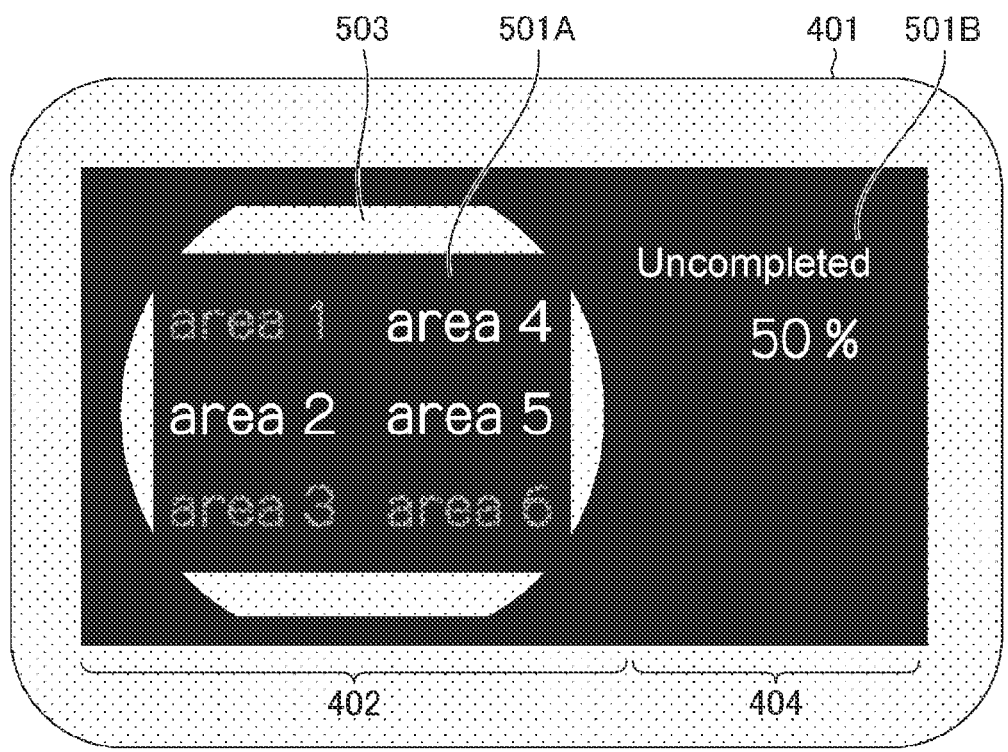
FIG. 17 is a diagram for describing an example of the case of displaying different observation state indications in the main display region and the sub display region.

FIG. 16 and FIG. 17 are diagrams for describing examples of the case of displaying different observation state indications in the main display region and the sub display region.

In the example illustrated in FIG. 16, the observation state indication 501A, having details indicating small areas that are listed, is provided in the main display region 402. In the sub display region 404, the observation state indication 501B of the photographic subject model M is displayed.

In the example illustrated in FIG. 17, the observation state indication 501A, having details indicating small areas that are listed, is provided in the main display region 402. In the sub display region 404, the observation state indication 501B indicating a percentage of incompletion of observation is displayed.

As illustrated in FIG. 16 and FIG. 17, in the main display region 402, the observation state indication 501A, which makes it possible to grasp the observation states of small area units in detail and which indicates small areas in a list view, is displayed upon the observation state of the photographic subject being changed. Accordingly, the user is able to grasp the detailed observation state of the photographic subject when the number of small areas for which observation has been completed increases. In the sub display region 404, the observation state indication 501B, which indicates the photographic subject model M or a percentage of incompletion of observation, is constantly displayed. Accordingly, the user is able to grasp an overview of the observation state of the photographic subject even in a case where the observation state indication 501A is not displayed in the main display region 402. In the above-described example, a description has been given of the monitor 401 having the main display region (first display region) 402 and the sub display region (second display region) 404. Alternatively, for example, the observation state indication 501 may be displayed on a monitor having a third display region. Alternatively, the observation state indication 501 may be provided on a plurality of monitors.

Other Examples

In the above description, a description has been given of the manner of providing the observation state indication 501 for the period of a predetermined display time. However, the manner of hiding the once displayed observation state indication 501 is not limited thereto.

For example, the display control unit 224 may hide the observation state indication 501 on the basis of an instruction input by a user via the handheld operation section 102 (user operation acceptance unit) (see FIG. 1). Furthermore, the display control unit 224 may display again the once hidden observation state indication 501 on the basis of an instruction input by a user via the handheld operation section 102 (user operation acceptance unit). In this way, as a result of controlling displaying and hiding of the observation state indication 501 by the user using the handheld operation section 102, the user is able to check the observation state indication at a desired timing.

Examples of the present invention have been described above. The present invention is not limited to the above-described embodiment, and various modifications can be made without deviating from the spirit of the present invention.

REFERENCE SIGNS LIST 10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
141 air/water supply button
142 suction button
143 function button 144 imaging button
170 light guide
200 endoscope processor apparatus
202 image input controller
204 image processing unit
205 communication control unit
206 video output unit
207 recording unit
208 operation unit
209 audio processing unit
209A speaker
210 CPU
211 ROM
212 RAM
220 medical image acquiring unit
222 observation state determining unit
224 display control unit
232A input layer
232B intermediate layer
232C output layer
234 convolutional layer
235 pooling layer
236 fully connected layer
300 light source apparatus
310 light source
310B blue light source
310G green light source
310R red light source
310V violet light source
330 diaphragm
340 condenser lens
350 light source control unit
400 monitor

What is claimed is:

1. A medical image processing apparatus comprising one or more processors and one or more memories,
the one or more processors being configured to:
acquire a plurality of medical images in a time-series manner;
make a determination of an observation state of each of a plurality of predetermined areas in an organ of a photographic subject positioned differently from each other, using the plurality of medical images, to determine that the observation state is observation-completed in a case where observation is completed and determine that the observation state is observation-uncompleted in a case where observation is uncompleted;
display, on a monitor, a notification that the observation state of each of the plurality of predetermined areas of the photographic subject is observation-uncompleted or observation-completed, on the basis of a result of the determination;
cause the one or more memories to store the result of the determination; and
update, in a case where the observation state of any one of the plurality of areas of the photographic subject changes from observation-uncompleted to observation-completed, a display on the monitor to inform that the observation state of the one area is the observation-completed.

2. The medical image processing apparatus according to claim 1, wherein the processor is configured to cause an observation state indication displayed on the monitor to be hidden after a predetermined time elapses.

3. The medical image processing apparatus according to claim 1, further comprising a user operation acceptance unit, wherein
the processor is configured to cause an observation state indication to be displayed or hidden on the basis of an instruction from the user operation acceptance unit.

4. The medical image processing apparatus according to claim 1, wherein the processor is configured to, in a case of determining an observation state in units of a small area of the photographic subject on the basis of the medical images, determine that observation is completed in a case where observation of the small area has been completed, and determine that observation is uncompleted in a case where observation of the small area has not been completed.

5. The medical image processing apparatus according to claim 1, wherein the processor is configured to cause the monitor to display an observation state indication by using text information.

6. The medical image processing apparatus according to claim 5, wherein the processor is configured to provide the text information with information regarding completion or incompletion of observation of units of a small area of the photographic subject, and cause the monitor to display, as the observation state indication, the text information provided with the information.

7. The medical image processing apparatus according to claim 1, wherein the processor is configured to cause an observation state indication to be displayed by using a photographic subject model schematically representing the photographic subject.

8. The medical image processing apparatus according to claim 7, wherein the processor is configured to provide the photographic subject model with information regarding completion or incompletion of observation of units of a small area of the photographic subject, and cause the monitor to display, as the observation state indication, the photographic subject model provided with the information.

9. The medical image processing apparatus according to claim 1, wherein the processor is configured to cause the monitor to display, as an observation state indication, an indication indicating only completion of observation of units of a small area of the photographic subject or an indication indicating only incompletion of observation of the unit of the small area of the photographic subject.

10. The medical image processing apparatus according to claim 1, wherein the processor is configured to cause the monitor to display the medical images such that an observation state indication is superimposed on the medical images.

11. The medical image processing apparatus according to claim 1, wherein the processor is configured to cause a monitor having a first display region and a second display region smaller than the first display region to display an observation state indication in the first display region and the second display region in a manner different between the first display region and the second display region.

12. The medical image processing apparatus according to claim 11, wherein the processor is configured to cause the observation state indication to be constantly displayed in the second display region.

13. The medical image processing apparatus according to claim 11, wherein the processor is configured to cause a monitor having the first display region and a third display region different from the second display region to display the medical images in the third display region.

14. The medical image processing apparatus according to claim 1, wherein the one or more processors are configured to make the determination of the observations state with a trained model which are learned to recognize each of the plurality of the areas.

15. A medical image processing method for a medical image processing apparatus comprising one or more processors and one or more memories, the one or more processors being configured to execute:

a medical image acquisition step of acquiring a plurality of medical images in a time-series manner;

an observation state determination step of making a determination of an observation state of each of a plurality of predetermined areas in an organ of a photographic subject positioned differently from each other, using the plurality of medical images, to determine that the observation state is observation-completed in a case where observation is completed and determine that the observation state is observation-uncompleted in a case where observation is uncompleted;

a display step of displaying, on a monitor, a notification that the observation state of each of the plurality of predetermined areas of the photographic subject is observation-uncompleted or observation-completed, on the basis of a result of the determination;

a storage step of causing the one or more memories to store the result of the determination; and an update step of updating, in a case where the observation state of any one of the plurality of areas of the photographic subject changes from observation-uncompleted to observation-completed, a display on the monitor to inform that the observation state of the one area is the observation-completed.

16. A non-transitory computer-readable tangible recording medium storing a program which causes, when read by a computer, the computer to execute the medical image processing method according to claim 15.

* * * * *